(12) United States Patent
Rust et al.

(10) Patent No.: US 9,096,364 B2
(45) Date of Patent: Aug. 4, 2015

(54) CONTAINER FOR A MEDICAL DEVICE

(71) Applicants: Michael Rust, Springfield, MA (US); James Nichols, Franklin, TN (US); Nicholas Carlson, Great Barrington, MA (US)

(72) Inventors: Michael Rust, Springfield, MA (US); James Nichols, Franklin, TN (US); Nicholas Carlson, Great Barrington, MA (US)

(73) Assignee: WESTERN NEW ENGLAND UNIVERSITY, Springfield, MA (US)

( * ) Notice: Subject to any disclaimer, the term of this patent is extended or adjusted under 35 U.S.C. 154(b) by 315 days.

(21) Appl. No.: 13/743,636

(22) Filed: Jan. 17, 2013

(65) Prior Publication Data

US 2013/0193130 A1 Aug. 1, 2013

Related U.S. Application Data

(60) Provisional application No. 61/592,080, filed on Jan. 30, 2012.

(51) Int. Cl.
| | | |
|---|---|---|
| *H05B 1/00* | (2006.01) | |
| *F23Q 7/00* | (2006.01) | |
| *A21B 1/22* | (2006.01) | |
| *F27D 11/00* | (2006.01) | |
| *B65D 81/18* | (2006.01) | |
| *A45C 11/24* | (2006.01) | |
| *A45C 13/02* | (2006.01) | |

(Continued)

(52) U.S. Cl.
CPC ............... *B65D 81/18* (2013.01); *A45C 11/24* (2013.01); *A45C 13/02* (2013.01); *A45C 2011/007* (2013.01); *A45C 2013/026* (2013.01); *A61B 5/14532* (2013.01); *Y10T 29/49002* (2015.01)

(58) Field of Classification Search
CPC ........ B65D 81/18; A45C 11/24; A45C 13/02; A45C 2011/007; A45C 2013/026; Y10T 29/49002; A61B 5/14532
USPC ......... 219/221, 214, 227, 228, 229, 260, 262, 219/263, 264, 265, 267, 268, 269, 385, 386, 219/387, 391, 393, 395, 396, 397, 399, 402, 219/403, 404, 406, 407, 408, 409, 410, 412, 219/413, 414, 429, 430, 432, 433, 434, 435, 219/436, 437, 438, 439, 441, 442, 219/443.1–553; 206/438, 440, 441, 63.3, 206/63.5, 828; 600/319, 316, 347, 365; 62/371, 457.1, 457.7, 457.9, 463, 464, 62/530

See application file for complete search history.

(56) References Cited

U.S. PATENT DOCUMENTS 3,218,955 A * 11/1965 Lorang ............................ 99/282
3,231,717 A * 1/1966 Moorhead ..................... 219/441

(Continued)

*Primary Examiner* — Sang Y Paik
*Assistant Examiner* — Gyounghyun Bae
(74) *Attorney, Agent, or Firm* — Cantor Colburn LLP

(57) ABSTRACT

A container for a medical device such as a glucose meter is provided. The container includes a base member having a plurality of sides defining an interior volume. A cover member is operably coupled to the base member and movable between a first position and a second position, wherein the cover member encloses the interior volume when in the second position. An insert is disposed within the interior volume, the insert having an opening sized to receive the glucose meter. A heating element is disposed within the opening. A thermostat is in thermal communication with the opening and electrically coupled to the heating element, wherein the thermostat is configured to flow electrical power to the heating element when a temperature within the interior volume is below a threshold.

15 Claims, 4 Drawing Sheets

(51) Int. Cl.
*A61B 5/145* (2006.01)
*A45C 11/00* (2006.01)

(56) References Cited

U.S. PATENT DOCUMENTS

| | | | | |
|---|---|---|---|---|
| 4,007,367 A | * | 2/1977 | Rusteberg et al. | 219/385 |
| 4,250,998 A | * | 2/1981 | Taylor | 206/570 |
| 4,322,954 A | * | 4/1982 | Sheehan et al. | 62/371 |
| 4,738,364 A | * | 4/1988 | Yeager | 206/563 |
| 4,852,471 A | * | 8/1989 | Lansing | 99/330 |
| 4,955,480 A | * | 9/1990 | Sexton | 206/528 |
| 5,130,706 A | * | 7/1992 | Van Steenwyk | 340/854.6 |
| 5,390,791 A | * | 2/1995 | Yeager | 206/438 |
| 5,704,223 A | * | 1/1998 | MacPherson et al. | 62/3.62 |
| 5,828,810 A | * | 10/1998 | Frank et al. | 392/502 |
| 5,935,468 A | * | 8/1999 | Nishino et al. | 219/438 |
| 6,093,156 A | * | 7/2000 | Cunningham et al. | 600/573 |
| 6,253,570 B1 | * | 7/2001 | Lustig | 62/457.2 |
| 7,597,196 B2 | * | 10/2009 | Langone | 206/438 |
| 7,626,142 B2 | * | 12/2009 | Backus et al. | 219/403 |
| 8,550,251 B1 | * | 10/2013 | Ford | 206/570 |
| 2006/0174648 A1 | * | 8/2006 | Lantz | 62/371 |
| 2008/0290081 A1 | * | 11/2008 | Biddell | 219/203 |
| 2010/0282762 A1 | * | 11/2010 | Leonard | 220/592.01 |
| 2010/0319627 A1 | * | 12/2010 | Cauchy et al. | 119/500 |
| 2011/0232303 A1 | * | 9/2011 | Whewell, Jr. | 62/62 |

* cited by examiner

CONTAINER FOR A MEDICAL DEVICE

BACKGROUND OF THE INVENTION

The subject matter disclosed herein relates to a container for a medical device and in particular to a container that maintains a hand-held glucose meter at a desired temperature operating range during storage and transport.

Blood glucose measurements are vital for a wide range of medical purposes. Traditionally, glucose meters have been used in fixed facilities having controlled environmental conditions, such as at a hospital or a doctor's office for example. Increasingly, handheld glucose meters are being used outside of the hospital in ambulatory environments. This provides advantages in obtaining measurement from a patient, allowing for a faster response by medical personnel.

The use of a glucose meter by ambulance or other medical responders exposes the meter to colder temperatures, especially in northern climates. Typically, a hand glucose meter is expected to operate in the range of 15° C.-40° C. Unfortunately, the average temperature in a northern climate, such as Massachusetts for example, may have an average temperature of about 5° C. between the months of September-March. The outdoor storage and operation of the glucose meter sometimes results in the temperature of the glucose meter dropping below the desired operating range of the sensors within the meter. In order to prevent inaccuracies, producers of glucose meters have included temperature sensors that give an error message and disable the meter when temperature sensor detects a temperature that is lower then the desired operating range. During transit in an ambulance from the hospital to the patient's location, the temperature of the glucose meter may drop rendering it inoperable at the patient's location.

Accordingly, while existing glucose meter containers are suitable for their intended purposes the need for improvement remains, particularly in providing a container for glucose meters that maintains the glucose meter at a desired operating range during cold weather.

BRIEF DESCRIPTION OF THE INVENTION

According to one aspect of the invention, a container for a glucose meter is provided. The container includes a base member having a plurality of sides defining an interior volume. A cover member is operably coupled to the base member and movable between a first position and a second position, wherein the cover member encloses the interior volume when in the second position. An insert is disposed within the interior volume, the insert having an opening sized to receive the glucose meter. A heating element is disposed within the opening. A thermostat is arranged in thermal communication with the opening and electrically coupled to the heating element, wherein the thermostat is configured to flow electrical power to the heating element when a temperature within the interior volume is below a threshold.

According to another aspect of the invention, another container for a glucose meter is provided. A base member having a plurality of sides defining an interior volume. A cover member is operably coupled to the base member and movable between a first position and a second position, wherein the cover member encloses the interior volume when in the second position. An insert is disposed within the interior volume, the insert having a first opening sized to receive the glucose meter, and a second opening disposed adjacent the first opening. A heating element is disposed within the opening. A thermostat is arranged in thermal communication with the opening and electrically coupled to the heating element, wherein the thermostat is configured to energize the heating element when a temperature within the interior volume is below a threshold. An energy source is electrically coupled to the thermostat and the heating element, the energy source being disposed in the second opening.

According to yet another aspect of the invention, a method of maintaining a glucose meter within a predetermined operating temperature is provided. The method includes providing a container having an interior volume, the container having a cover member arranged to move between an open and a closed position. An insert is disposed within the interior volume, the insert having an opening therein. A heating element is electrically coupled to an energy source by a thermostat, the heating element being disposed within the opening, the opening sized to receive the glucose meter. The thermostat is configured to close when the temperature within the opening is below a threshold. The heating element is configured to energize when the thermostat is in the closed position.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Handheld glucose meters are a commonly used medical analytical device used by medical personnel and patients to determine a patient's blood glucose level. In patients having certain medical conditions, such as diabetes, monitoring of glucose levels is important daily activity to prevent hypoglycemia (insulin levels too low) and hyperglycemia (insulin level too high). The accuracy of the glucose meter may decline when the temperature falls below the desired operating range. Embodiments of the present invention provide advantages in maintaining a handheld glucose meter above a low temperature threshold when the glucose meter is being stored or during transportation.

Figure 1:
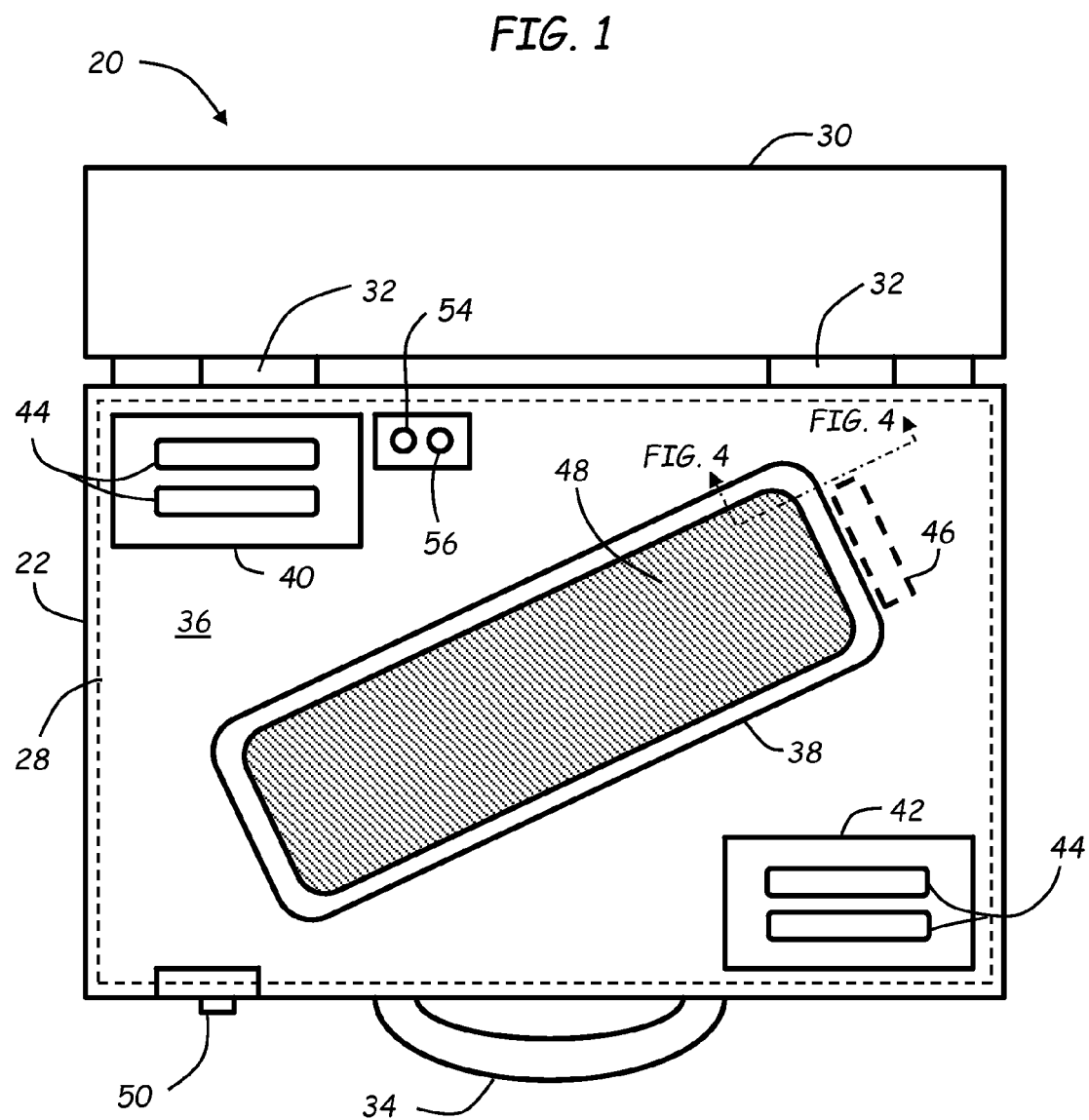
FIG. 1 is top view of a container for a glucose meter in accordance with an embodiment of the invention.
Figure 2:
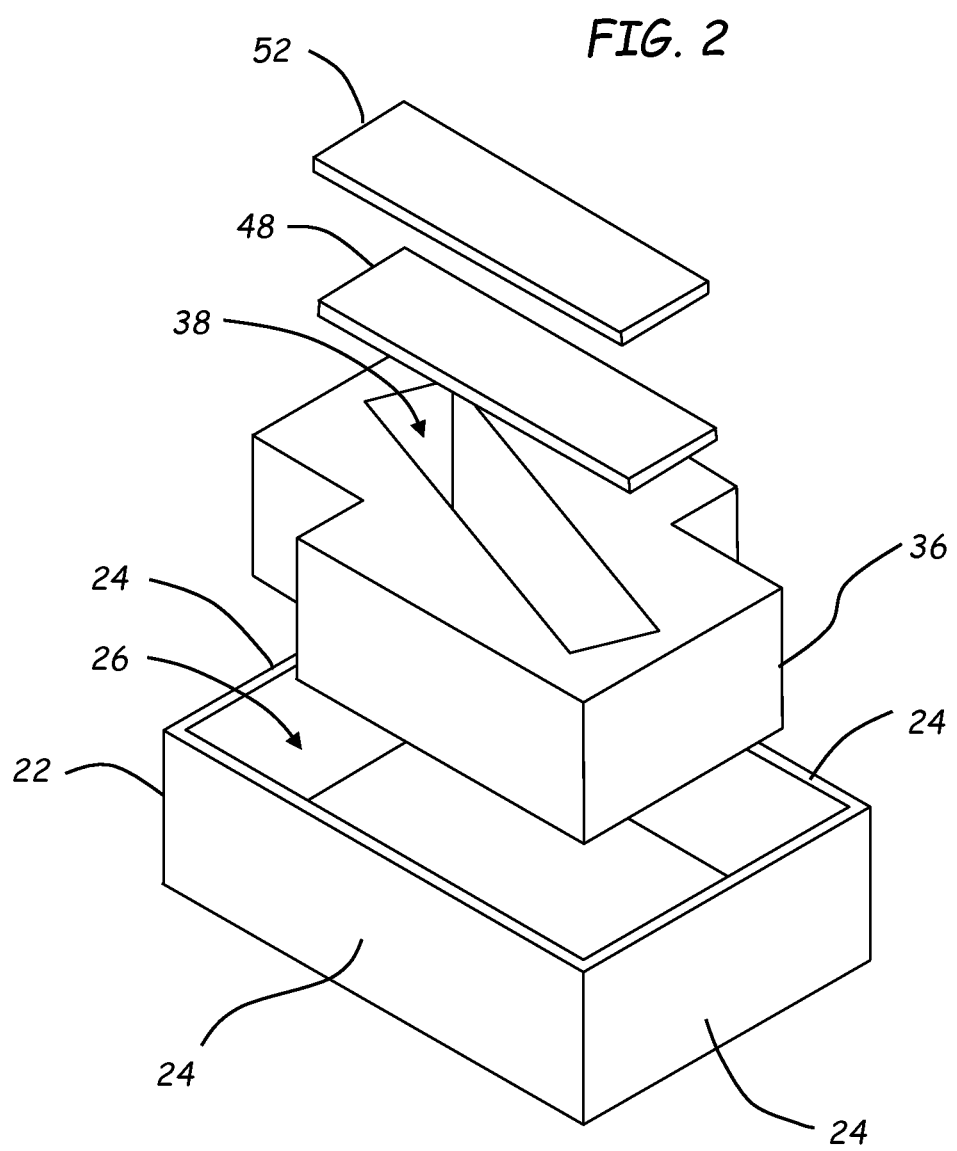
FIG. 2 is a partial exploded view of the container of FIG. 1.
Figure 3:
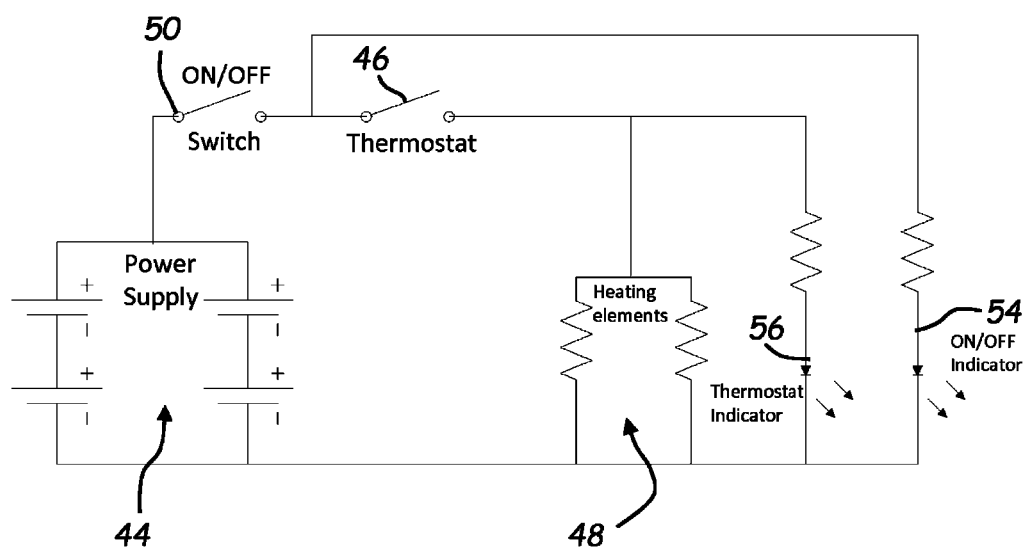
FIG. 3 is a schematic diagram of a circuit for use with the container of FIG. 1.
Figure 4:
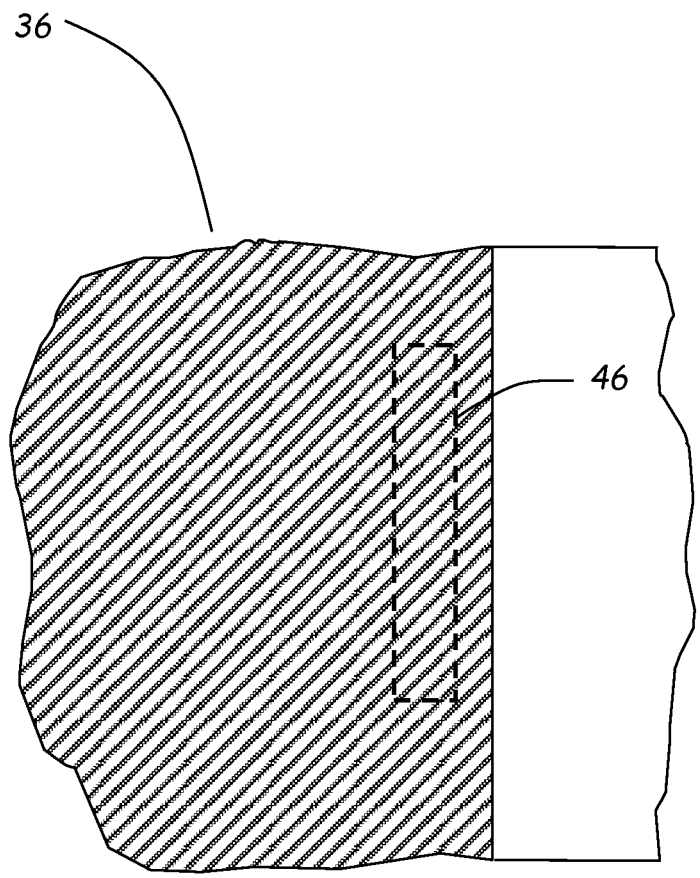
FIG. 4 is a partial side sectional view of the container of FIG. 1.

Referring to FIG. 1-FIG. 3, a container 20 is shown that is configured to store a handheld glucose meter. The container 20 includes a base member 22 having a plurality of side walls 24 disposed about a periphery of the base in a generally parallelepiped shape. The side walls 24 define an interior volume 26. In the exemplary embodiment, the base member 22 is made from a substantially rigid plastic material such as acrylonitrile butadiene styrene (ABS) for example. In one embodiment, the base may include a seal 28, such as a neoprene o-ring for example, disposed on or adjacent to the end of the side walls 24.

The container 20 further includes a cover member 30 rotationally coupled to the base member 22 by one or more hinges 32. The cover member 30 is movable between an open position and a closed position. When in the closed position, the cover member 30 may engage the seal 28 to provide a water tight seal to protect the glucose meter. In the exemplary embodiment, the cover member 30 is made from a substantially rigid plastic material such as ABS for example. The base member 22 and cover member 30 may further include a latching mechanism (not shown) that securely holds the cover member 30 in the closed position and prevents inadvertent opening of the container. The base member 22 and cover member 30 may further include a handle 34 disposed on one side to assist the user in transporting the glucose meter.

Disposed within the interior volume 26 is an insert 36. The insert 36 may be an open-cell or a closed-cell foam material such as a polyurethane "pluck foam" material for example. The insert 36 has a first opening 38 sized to receive a handheld glucose meter. In the exemplary embodiment, the first opening 38 is 2 inches (50.8 millimeters) wide and 7 inches (177.8 millimeters) long. In one embodiment, the first opening 38 is arranged on an angle to the side walls 24. In another embodiment, the first opening 38 is arranged generally perpendicular to the ends of the base member 22. In one embodiment, the first opening 38 includes a layer of foam material (not shown) at the bottom of the first opening 38 (e.g. opposite the cover member 30). It should be appreciated that the size of the first opening 38 may be changed to accommodate different model glucose meters. In other embodiments, the insert 36 may be comprised of a plurality of inserts that allows the first opening 38 to be changed or adapted to different model glucose meters.

Arranged adjacent to the first opening 38 are a second opening 40 and an opposing third opening 42. The openings 40, 42 are sized to receive an energy source, such as batteries 44. In the exemplary embodiment, the energy source is capable of generating an output of 3V. In one embodiment, the energy source comprises four D-cell type dry-cell batteries arranged as two sets of two batteries. The placement of the batteries 44 in opposite corners provides advantages in balancing the container 20. It should be appreciated that a balanced container 20 facilitates the carrying of the container 20 by the user.

Also adjacent the first opening 38 is a temperature sensor, such as thermostat 46 for example. The thermostat 46 may be a suitable temperature sensor capable of switching on and off electrical power from the energy source 44. Therefore, the thermostat 46 may be a bimetallic mechanical or electrical sensor; an expanding wax pellet type sensor; an electronic thermistor; a thermocouple; or a semiconductor device for example. In the exemplary embodiment, the thermostat 46 is an in-line type thermostat having a temperature operating range of 20° C.±3° C. The thermostat 46 is electrically coupled between the energy source 44 and a heating device 48. The heating device 48 is disposed in the first opening 38 opposite the cover member 30. The heating device 48 is electrically coupled to the energy source 44, the thermostat 46 and a switch 50. In one embodiment, the switch 50 is mounted to the base member 22 with an actuator portion extending through the wall of the base member 22 allowing the user to turn the heating device 48 on or off without opening the container 20. In one embodiment, the switch 50 is arranged to be actuated by the cover member 30 such that the heating element is activated each time the container 20 is closed.

In the exemplary embodiment, the heating device 48 has a generally rectangular shape with a relatively thin thickness. In one embodiment, the heating device 48 is sized to fit and substantially fill the first opening 38. The heating device 48 may be a suitable device capable of maintaining the area within the first opening at a temperature above a desired threshold, such as 20° C. for example, during operation. The heating device 48 may be a resistive heating element for example that generates heat in response to the application of electrical current. Therefore, the heating device 48 may be radiative heater, a convection heater or a conductive heater for example. The heating device 48 may also incorporate a fan to circulate air within the first opening 38. In one embodiment, the heating device 48 may be enclosed within a thin highly conductive metal member 52, such as a foil member having a thickness between 0.015 millimeters to 0.025 millimeters and made from aluminum. The metal member 52 provides advantages in improving the distribution of heat generated by the heating device 48.

In one embodiment, the container 20 further includes a pair of light emitting diodes (LED). The first LED 54 is electrically coupled between the switch 50 and the energy source 44. In this arrangement, the first LED 54 emits light when the switch is in an "on" position, thus providing an indication to the user that the container 20 is operating. The second LED 56 is electrically coupled between the thermostat 46 and the energy source 44. In this arrangement, the second LED 56 emits light when the thermostat 46 is providing electrical power to the heating device 48. The second LED 56 provides an indicator to the user when the heating device 48 is operating. In one embodiment, the LED's 54, 56 are arranged within the base member 22. In another embodiment, the LED's 54, 56 are mounted to either the base member 22 or the cover member 30 and extend through the wall allowing the LED's 54, 56 to be seen by the user when the container 20 is closed.

In operation, the user places a medical instrument, such as a handheld glucose meter for example, into the first opening 38. After closing and securing the cover member 30, user moves the actuator or switch 50 to the "on" position. This allows electrical power to flow from the energy source 44 to the thermostat 46. In the exemplary embodiment, the thermostat 46 switches to the "on" position, meaning electrical power may flow to the heating device 48, at a temperature of 15° C. The thermostat device 48 then switches to the "off" position when the temperature increases to greater than 15° C. In another embodiment, the thermostat switches to the "on" position at 17° C. and the "off" position at 23° C. Accordingly, with the switch 50 in the "on" position, the container 20 will maintain the glucose meter at above a threshold operating temperature.

It should be appreciated that embodiments of the present invention provide advantages in maintaining a medical device, such as a hand-held glucose meter, within a desired temperature range during transportation and storage. Embodiments of the present invention further provide advantages in improving the accuracy of medical devices, such as hand-held glucose meters, when used in cold environments. Embodiments of the present invention provide yet further advantages in protecting medical devices, such as hand-held glucose meters, during transportation and storage.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A container for a glucose meter comprising:
   a base member having a plurality of sides defining an interior volume;
   a cover member rotationally coupled to the base member by a hinge member and movable between a first position and a second position, wherein the cover member encloses the interior volume when in the second position;
   a seal member disposed between the cover member and the base member adjacent the sides of the base member;
   A latch member selectively coupling the base member to the cover member;
   an insert disposed within the interior volume, the insert having an opening sized to receive the glucose meter;
   a heating element disposed within and substantially fill a bottom end of the opening and is in direct thermal contact with the glucose meter under the cover member; and,
   a thermostat in thermal communication with the opening and electrically coupled to the heating element, wherein the thermostat is configured to flow electrical power to the heating element when a temperature within the interior volume is below a threshold.

2. The container of claim 1 further comprising a switch coupled to the base, the switch having an actuator extending through one of the plurality of sides opposite the interior volume, the switch being electrically coupled to the thermostat and heating element.

3. The container of claim 2 further comprising at least one energy source disposed within the interior volume, the energy source being electrically coupled to the thermostat.

4. The container of claim 3 further comprising a first light emitting diode (LED) electrically coupled to the thermostat.

5. The container of claim 4 further comprising a second LED electrically coupled to the switch.

6. The container of claim 1 wherein the heating element is a resistance heater.

7. The container of claim 1 further comprising a foil member disposed above the resistance heater within the first opening.

8. A container for a glucose meter comprising:
   a base member having a plurality of sides defining an interior volume;
   a cover member operably coupled to the base member and movable between a first position and a second position, wherein the cover member encloses the interior volume when in the second position;
   an insert disposed within the interior volume, the insert having a first opening sized to receive the glucose meter, and a second opening disposed adjacent the first opening;
   a heating element disposed within the opening;
   a foil element disposed on a surface of the heating element;
   a thermostat in thermal communication with the opening and electrically coupled to the heating element, wherein the thermostat is configured to energize the heating element when a temperature within the interior volume is below a threshold;
   an energy source electrically coupled to the thermostat and the heating element, the energy source being disposed in the second opening;
   a switch electrically coupled between the thermostat and the energy source, the switch being disposed to be actuated when the cover in the second position; and
   a first LED electrically coupled between the thermostat and the heating element, and a second LED electrically coupled between the switch and the thermostat.

9. The container of claim 8 wherein the energy source includes a first battery arrangement having an output of 3V.

10. The container of claim 9 wherein the insert includes a third opening adjacent the first opening opposite the second opening.

11. The container of claim 10 wherein the energy source includes second battery arrangement, the first battery arrangement and the second battery arrangement having an output of 3V.

12. The container of claim 11 further comprising a switch electrically coupled between the thermostat and the energy source, the switch being disposed to be actuated when the cover in the second position.

13. A container for a glucose meter comprising:
   a base member having a plurality of sides defining an interior volume;
   a cover member operably coupled to the base member and movable between a first position and a second position, wherein the cover member encloses the interior volume when in the second position;
   an insert disposed within the interior volume, the insert having a first opening sized to receive the glucose meter, and a second opening disposed adjacent the first opening, wherein the insert includes a third opening adjacent the first opening opposite the second opening;
   a heating element disposed within the opening;
   a thermostat in thermal communication with the opening and electrically coupled to the heating element, wherein the thermostat is configured to energize the heating element when a temperature within the interior volume is below a threshold;
   an energy source electrically coupled to the thermostat and the heating element, the energy source being disposed in the second opening, wherein the energy source includes a first battery and a second battery arrangement having an output of 3V;
   a switch electrically coupled between the thermostat and the energy source, the switch being disposed to be actuated when the cover in the second position; and
   a first LED electrically coupled between the thermostat and the heating element, and a second LED electrically coupled between the switch and the thermostat.

14. The container of claim 13 further comprising a metal foil member disposed about the heating element.

15. The container of claim 14 wherein the heating element is a resistance heater.

* * * * *